United States Patent
Stopp et al.

(10) Patent No.: US 11,989,915 B2
(45) Date of Patent: May 21, 2024

(54) INTRA-OPERATIVE DETERMINATION OF A FOCAL LENGTH OF A CAMERA FOR MEDICAL APPLICATIONS

(71) Applicant: Brainlab AG, Munich (DE)

(72) Inventors: Sebastian Stopp, Munich (DE); Johannes Zügner, Munich (DE); Johannes Manus, Munich (DE); José Gardiazabal, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 18/317,585

(22) Filed: May 15, 2023

(65) Prior Publication Data
US 2023/0281874 A1 Sep. 7, 2023

Related U.S. Application Data

(63) Continuation of application No. 17/275,052, filed as application No. PCT/EP2019/074155 on Sep. 11, 2019, now Pat. No. 11,694,363.

(30) Foreign Application Priority Data

Sep. 12, 2018 (WO) .................. PCT/EP2018/074664

(51) Int. Cl.
*G06T 7/00* (2017.01)
*A61B 34/00* (2016.01)
(Continued)

(52) U.S. Cl.
CPC .............. *G06T 7/80* (2017.01); *A61B 34/20* (2016.02); *A61B 34/25* (2016.02); *A61B 90/39* (2016.02);
(Continued)

(58) Field of Classification Search
CPC ....... G06T 7/80; G06T 7/246; G06T 2200/24; G06T 2207/30004; G06T 2207/30204;
(Continued)

(56) References Cited

U.S. PATENT DOCUMENTS 4,398,811 A * 8/1983 Nishioka ............ G02B 23/2407
                                                              385/117
4,622,954 A * 11/1986 Arakawa .............. A61B 1/0051
                                                              600/153
(Continued)

FOREIGN PATENT DOCUMENTS

CN       106908041 A1    6/2017
JP       2014016309 A1   1/2014
(Continued)

OTHER PUBLICATIONS

International Preliminary Report on Patentability for corresponding International Application No. PCT/EP2019/074155, dated Oct. 11, 2019. 7 Pages.
(Continued)

*Primary Examiner* — Frank F Huang
(74) *Attorney, Agent, or Firm* — Tucker Ellis LLP

(57) ABSTRACT

A method of determining a focal length of a camera and/or of adjusting a viewing direction in a graphical representation of a pre-operative image is provided. The method includes providing uncalibrated camera data of a camera, specifying an initial value of a focal length of the camera, specifying a working distance value of a distance between the camera and the at least part of the tracking system, calculating a distance value of the distance between the camera and the at least part of the tracking system based on the uncalibrated camera data and based on the specified initial value of the focal length of the camera, calculating a change factor based on the specified working distance value and the calculated distance value, and calculating an adapted value of the focal
(Continued)

length of the camera based on the initial value of the focal length and based on the change factor.

18 Claims, 4 Drawing Sheets

(51) Int. Cl.
| | |
|---|---|
| A61B 34/20 | (2016.01) |
| A61B 90/00 | (2016.01) |
| G06T 7/246 | (2017.01) |
| G06T 7/80 | (2017.01) |
| H04N 17/00 | (2006.01) |
| H04N 23/67 | (2023.01) |

(52) U.S. Cl.
CPC ........... *G06T 7/246* (2017.01); *H04N 17/002* (2013.01); *H04N 23/67* (2023.01); *A61B 2034/2055* (2016.02); *A61B 2090/3937* (2016.02); *G06T 2200/24* (2013.01); *G06T 2207/30004* (2013.01); *G06T 2207/30204* (2013.01)

(58) Field of Classification Search
CPC ......... A61B 34/20; A61B 34/25; A61B 90/39; A61B 2034/2055; A61B 2090/3937; A61B 90/361; H04N 5/23212; H04N 17/002
See application file for complete search history.

(56) References Cited

U.S. PATENT DOCUMENTS

| | | | | |
|---|---|---|---|---|
| 4,905,082 | A * | 2/1990 | Nishigaki | A61B 1/07 600/109 |
| 5,557,454 | A * | 9/1996 | Takahashi | G02B 23/2415 348/45 |
| 6,025,873 | A * | 2/2000 | Nishioka | G02B 23/26 600/181 |
| 6,256,058 | B1 | 7/2001 | Kang et al. | |
| 6,362,877 | B1 * | 3/2002 | Kobayashi | G01R 31/281 356/614 |
| 6,434,416 | B1 | 8/2002 | Mizoguchi | |
| 6,537,208 | B1 * | 3/2003 | Konno | H04N 5/2253 348/340 |
| 2002/0163742 | A1 * | 11/2002 | Togino | G02B 17/02 359/837 |
| 2003/0097044 | A1 * | 5/2003 | Rovegno | A61B 1/07 600/173 |
| 2005/0085698 | A1 * | 4/2005 | Bonningue | A61B 1/00183 600/129 |
| 2005/0197533 | A1 * | 9/2005 | May | A61B 1/042 600/137 |
| 2009/0292170 | A1 * | 11/2009 | Boebel | G02B 23/2415 600/111 |
| 2014/0071444 | A1 * | 3/2014 | Matsumoto | G01N 21/954 356/241.1 |
| 2014/0267626 | A1 | 9/2014 | Lilagan | |
| 2016/0255324 | A1 * | 9/2016 | Kazakevich | G02B 23/2484 348/43 |
| 2016/0357007 | A1 * | 12/2016 | Swanson | G01B 9/02028 |
| 2018/0367786 | A1 * | 12/2018 | Furst | G01J 3/027 |
| 2023/0260158 | A1 * | 8/2023 | Stopp | A61B 34/20 382/128 |

FOREIGN PATENT DOCUMENTS

| | | |
|---|---|---|
| KR | 20150124069 A1 | 11/2015 |
| WO | 2014083386 A2 | 6/2014 |
| WO | 2017108417 A1 | 6/2017 |
| WO | 2017134915 A1 | 8/2017 |

OTHER PUBLICATIONS

International Preliminary Report on Patentability for corresponding International Application No. PCT/EP2019/074155, dated Mar. 25, 2021, 8 Pages.
Wang et al. "DodecaPen: Accurate 6DoF Tracking of a Passive Stylus. Media IC System Lab". Oculus Research. 2017. 10 pages.
Hartley et al., "Multiple View Geometry in Computer Vision". Accessible online at https://www.cambridge.org/core/books/multiple-view-geometry-in-computer-vision/0B6F289C78B2B23F596CAA76D3D43F7A. 2004. 1 Page.
Garrido-Jurado et al. "Automatic generation and detection of highly reliable fiducial markers under occlusion". Computing and Numerical Analysis department, University of Cordoba. 2014. 15 Pages.

* cited by examiner

INTRA-OPERATIVE DETERMINATION OF A FOCAL LENGTH OF A CAMERA FOR MEDICAL APPLICATIONS

RELATED APPLICATION DATA

This application is a continuation of U.S. patent application Ser. No. 17/275,052 filed Mar. 10, 2021, which is a national phase application of International Application No. PCT/EP2019/074155 filed Sep. 11, 2019, which claims priority to International Application No. PCT/EP2018/074664, filed on Sep. 12, 2018, the contents of both of which are incorporated herein by reference.

FIELD OF THE INVENTION

The present invention relates to a computer-implemented method, e.g. a medical method, of intra-operatively determining a focal length of a camera. Alternatively or additionally, the present invention relates to a computer-implemented method, e.g. a medical method, for adjusting a viewing direction in a graphical representation of a pre-operative image, particularly a three-dimensional image or scan, of at least a part of a patient. The invention further relates to a corresponding computer program, a non-transitory program storage medium storing such a program and a computer for executing the program, as well as a medical system comprising an electronic data storage device and the aforementioned computer.

TECHNICAL BACKGROUND

In many operating rooms or operating theatres a two-dimensional standard camera, i.e. a camera not providing three-dimensional or depth information, but only acquiring two-dimensional camera data and/or two-dimensional images, is arranged, e.g. on a ceiling of the respective operating room. These standard cameras primarily serve to record images and/or a video of an operating procedure in order to document the operating procedure.

Usually, optical characteristics, such as e.g. lens parameters, a focal spot position and/or a value of the focal length (also referred to hereinafter as true or actual value of the focal length), of such standard camera of an operating room, are unknown. In other words, standard cameras installed in operating rooms usually provide uncalibrated camera data and/or usually are uncalibrated. Further, a determination of the optical characteristics usually requires a time-consuming calibration measurement, in which for example the lens parameters, the focal spot position and/or a value of the focal length of the respective camera can be determined.

For certain applications, however, such as for example tracking applications, in which preferably a three-dimensional information can be obtained and/or derived from two-dimensional images of a camera, an information about the optical characteristics of the camera may be desirable.

It may, therefore, be desirable to provide for an improved computer-implemented method for intra-operatively determining a focal length (or a value thereof) of a camera, which camera provides uncalibrated camera data. Likewise, it may be desirable to provide for an improved computer-implemented method for adjusting a viewing direction in a graphical representation of a pre-operative image of a patient.

The present invention can be used for tracking procedures e.g. in connection with a system for image-guided surgery such as CURVE, a product of Brainlab AG.

Aspects of the present invention, embodiments, examples, exemplary features and exemplary steps are disclosed in the following. Different aspects, embodiments, examples, exemplary features and exemplary steps of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method relates to a computer-implemented method, particularly a medical method, of intra-operatively determining a focal length of a camera.

Alternatively or additionally, the disclosed method relates to a computer-implemented method, particularly a medical method, for adjusting a viewing direction in a graphical representation of a pre-operative image of at least a part of a patient. Alternatively or additionally, the disclosed method relates to a computer-implemented method, particularly a medical method, of intra-operatively determining a focal length of a camera for adjusting a viewing direction in a graphical representation of a pre-operative image of at least a part of a patient.

Here and in the following, the term "intra-operatively" may mean that the method according to the invention can be performed during and/or simultaneously to an actual operation and/or surgery performed on a patient.

Further, the "pre-operative image" may refer to three-dimensional image data and/or image data set of the at least part of the patient. For example, the pre-operative image may be determined in a pre-operative scan using any imaging modality. Accordingly, the pre-operative image may refer to a computed tomography (CT) scan or image, a magnetic resonance (MR) scan or image, a three-dimensional ultrasound scan or image, or the like.

The disclosed method comprises providing uncalibrated camera data of a camera, wherein the uncalibrated camera data comprise an image of a tracking system. The camera may refer to an uncalibrated camera and/or a camera with unknown optical characteristics, such as e.g. unknown lens parameters, an unknown focal spot position, an unknown optical center, and/or an unknown value of the focal length. Accordingly, the term "uncalibrated camera data" may mean that the optical characteristics of the camera are unknown and/or that a reference system of the camera data is unknown.

The method further comprises specifying an initial value of a focal length of the camera and specifying a working distance value of a distance between the camera and the tracking system. Further, the method comprises calculating a distance value of the distance between the camera and the tracking system based on the uncalibrated camera data and based on the specified initial value of the focal length of the camera. Further, the method comprises calculating a change factor based on the specified working distance value and the calculated distance value, and calculating an adapted value of the focal length of the camera based on the initial value of the focal length and based on the change factor.

Generally, this allows to intra-operatively determine and/or estimate the value of the focal length of the camera. In turn, this allows to derive further information from the uncalibrated camera data, such as e.g. a three-dimensional information and/or a depth information, as will be further elucidated in the following.

GENERAL DESCRIPTION OF THE INVENTION

In this section, a description of the general features of the present invention is given for example by referring to possible embodiments of the invention.

As set out hereinabove, it may be desirable to provide for an improved computer-implemented method for intra-operatively determining a focal length (or a value thereof) of a camera, which camera provides uncalibrated camera data. Likewise, it may be desirable to provide for an improved computer-implemented method for adjusting a viewing direction in a graphical representation of a pre-operative image of a patient.

This is achieved by the subject-matter of the independent claims, wherein further embodiments are incorporated in the dependent claims and the following description.

According to a first aspect of the invention, there is provided a computer-implemented method of intra-operatively determining a focal length and/or a value thereof of a camera and/or for adjusting, e.g. intra-operatively adjusting, a viewing direction in a graphical representation of a pre-operative image, particularly a three-dimensional image or scan, of at least a part of a patient. The method comprises the following steps:

providing uncalibrated and/or non-calibrated camera data of a camera, wherein the uncalibrated camera data comprise an image of at least a part of a tracking system (e.g. positioned close to a region of interest of the patient), at least a part of a marker device of the tracking system, at least a part of a region of interest of the patient and/or at least a part of a working environment;

specifying and/or assuming an initial value of a focal length of the camera;

specifying and/or assuming a working distance value of a distance between the camera and the at least part of the tracking system;

calculating, computing and/or determining a distance value of the distance between the camera and the at least part of the tracking system, e.g. a marker device of the tracking system (and/or the at least part of the region of interest and/or at least a part of the working environment), based on the uncalibrated camera data and based on the specified initial value of the focal length of the camera;

calculating, computing and/or determining a change factor based on the specified working distance value and the calculated distance value; and calculating, computing and/or determining an adapted value of the focal length of the camera based on the initial value of the focal length and based on the change factor.

As noted above, the camera may be uncalibrated and/or optical characteristics of the camera, particularly a true or actual value of the focal length of the camera, may be unknown. By means of the inventive method, particularly by calculating the change factor and/or by calculating the adapted value of the focal length, the true or actual value of the focal length may be accurately estimated, approximated and/or determined. Accordingly, the adapted value of the focal length may represent an estimation and/or approximation of the actual value of the focal length. However, the adapted value of the focal length may substantially correspond to and/or may substantially be identical to the actual value of the focal length. Generally, determining the adapted value of the focal length substantially corresponding to and/or approximating the actual value of the focal length may advantageously allow to derive comprehensive information from the uncalibrated image data, such as for example three-dimensional information of an object comprised in the uncalibrated camera (or the respective image), particularly with respect to the camera. For instance, determining the adapted value of the focal length may advantageously allow to determine a relative position of the camera and the object and/or a relative orientation of the object with respect to the camera.

By way of example, the object may be or refer to at least a part of the tracking system, such as e.g. a marker device of the tracking system. Accordingly, by means of the inventive method, the relative position and/or orientation of the at least part of the tracking system can be accurately and precisely determined, although the true or actual value of the focal length of the camera is unknown. In turn, this allows utilizing the uncalibrated camera data for a tracking application, in which e.g. the relative position and/or orientation of the at least part of the tracking system is determined.

Apart from that, since uncalibrated camera data can be used, the time-consuming and costly procedure of calibrating the camera in order to determine the actual focal length can be avoided. In turn, this allows to retrofit and/or implement the inventive method in operating rooms and/or operating theatres without requiring modifications to existing hardware in the respective operating room, particularly without requiring any modification to the camera and/or replacement of the camera, e.g. by a stereo camera or the like.

The specified and/or assumed initial value of the focal length can be arbitrarily and/or automatically chosen. In other words, the initial value may have an arbitrary value and/or may be automatically chosen, e.g. by a computer performing one or more steps of the method. However, the initial value of the focal length may also be chosen from a certain interval of focal length values, which may represent realistic, expected and/or potential values of the focal length.

Here and in the following the distance between the camera and the at least part of the tracking system (and/or the at least a part of the marker device, the at least part of the region of interest and/or at least a part of a working environment) may refer to an orthogonal and/or shortest distance between the camera and the at least part of the tracking system (and/or the at least a part of the marker device, the at least part of the region of interest and/or at least a part of a working environment). The orthogonal and/or shortest distance may be measured e.g. along and/or substantially parallel to an optical axis of the camera. The optical axis of the camera may also be referred to in the following as z-axis. Accordingly, the distance between the camera and the at least part of the tracking system may be measured between an outer edge of the camera (or a center position of the camera) and an outer edge (or a center position) of the at least part of the tracking system, e.g. an outer edge (or center position) of a marker device of the tracking system.

Further, the specified and/or assumed working distance value of the distance between the camera and the at least part of the tracking system may refer to an arbitrarily and/or automatically chosen and/or selected value of the distance between the camera and the at least part of the tracking system. In other words, the working distance value may have an arbitrary value and/or may be automatically chosen, e.g. by a computer performing one or more steps of the method. Accordingly, the assumed working distance value may differ from an actual or true value of the distance. Further, the working distance value may be chosen from a certain interval of distance values, which may represent realistic, expected and/or potential values of the distance between the camera and the at least part of the tracking system. By way of example, the working distance value may be selected and/or arbitrarily selected from an interval of about 0.1 m to about 20 m, particularly from about 0.5 m to about 10 m, preferably from about 1 m to about 5 m.

The calculated distance value of the distance between the camera and the at least part of the tracking system may be calculated based on processing the uncalibrated camera data and based on the initial value of the focal length. In other words, the calculated distance value may be derived from the uncalibrated camera data taking into account the initial value of the focal length. However, for the calculation of the calculated distance value further image processing techniques may optionally be applied or utilized, such as e.g. a point correlation correlating certain pixels of the uncalibrated camera data or the like.

Generally, the change factor may refer to and/or denote a change value and/or a change quantity. Therein, the change factor may be derived from the calculated distance value and the specified working distance value. Further, by way of example, the change factor may be multiplied with the initial value of focal length, added to the initial value, subtracted from the initial value or the initial value may be divided by the change factor in order to calculate the adapted value of the focal length.

It should be noted that the focal length, the initial value of the focal length and/or the adapted value of the focal length may refer to the focal length, the initial value and/or the adapted value in at least one spatial direction, preferably in two and/or two orthogonal spatial directions, wherein the at least one spatial direction may be transverse and/or orthogonal to the optical axis of the camera (and/or the z-axis). Particularly, the focal length may refer to a two-dimensional focal length in a first direction and in a second direction, wherein both the first and the second directions are transverse and/or orthogonal to a z-direction and/or to a direction parallel to the optical axis of the camera. Further, the first direction may refer to an x-direction and/or may be orthogonal to the second direction, wherein the second direction may refer to a y-direction. In other words, the focal length may be measured in the first direction and in the second direction in a plane (e.g. an image plane) that is transverse and/or orthogonal to the optical axis of the camera. Accordingly, the focal length may have a first component in the first direction and a second component in the second direction. Likewise, the initial value of the focal length may have a first component in the first direction and a second component in the second direction. Further, also the adapted value of the focal length may have a first component in the first direction and a second component in the second direction.

The change factor may refer to a scalar that may be applied to both the first component and the second component of the initial value of the focal length. Alternatively, also the change factor may have a first component and a second component, wherein the first component of the change factor may be applied to the first component of the initial value of the focal length to calculate the first component of the adapted value of the focal length. Similarly, the second component of the change factor may be applied to the second component of the initial value of the focal length to calculate the second component of the adapted value of the focal length.

Moreover, it should be noted that the inventive method can be performed in real time and/or online during an actual surgery. In other words, the method can be performed intra-operatively. Accordingly, the camera may capture and/or acquire a sequence of uncalibrated camera data or data sets, each comprising an image of the at least part of the tracking system. For each camera data, each camera data set and/or each image of the camera, the method, as described above and in the following, can be performed, particularly without any delay noticeable by a user and/or a surgeon.

It should be noted, however, that the invention does not involve or in particular comprise or encompass an invasive step which would represent a substantial physical interference with a body of a patient requiring professional medical expertise to be carried out and entailing a substantial health risk even when carried out with the required professional care and expertise. Particularly, the invention does not involve or in particular comprise or encompass any surgical or therapeutic activity. The invention is instead directed as applicable to image processing. For this reason alone, no surgical or therapeutic activity and in particular no surgical or therapeutic step is necessitated or implied by carrying out the invention.

According to an embodiment of the invention, the camera is a standard operating room camera. Alternatively or additionally, the camera is a two-dimensional camera and/or a camera configured to generate two-dimensional camera data. Accordingly, the uncalibrated camera data may refer to two-dimensional data representing, describing and/or comprising a two-dimensional image of the at least part of the tracking system. The camera may, for instance, refer to a standard RGB (Red, Green, Blue) camera. The camera may, for example, be arranged in a center of an array of light emitting diodes or any other lighting. Such camera may be pre-installed in many operating rooms. As noted above, since the true value of the focal length of the camera, which is unknown, can be approximated, estimated and/or determined by means of the method according to the present invention, the method can be implemented and/or retrofit in operating rooms without any modification to the hardware and/or camera of the respective operating room.

According to an embodiment of the invention, the step of calculating the distance value and/or the step of computing the change factor comprises:

determining, computing and/or calculating a deviation of the calculated distance value with respect to the specified working distance value; and comparing the determined deviation to a threshold value, particularly a predetermined and/or pre-set threshold value, for the deviation of the calculated distance value with respect to the specified working distance value.

Therein, the deviation of the calculated distance value with respect to the specified working distance value may be determined based on a subtraction of these two values. Alternatively or additionally a ratio of the calculated distance value and the specified distance value may be determined for determining the deviation. Generally, determining the deviation and comparing this deviation to the threshold value may allow to determine whether the initial value of the focal length should be further adapted to more closely approximate the true or actual value of the camera's focal length. By way of example, the change factor and/or the adapted focal length value may be calculated if, particularly only if, the determined deviation reaches and/or exceeds the threshold value.

According to an embodiment of the invention, at least the following steps are repeated in an iteration process:

- calculating, computing and/or determining a distance value of the distance between the camera and the at least part of the tracking system based on the uncalibrated camera data and based on the specified initial value of the focal length of the camera;
- calculating, computing and/or determining a change factor based on the specified working distance value and the calculated distance value; and
- calculating, computing and/or determining an adapted value of the focal length of the camera based on the initial value of the focal length and based on the change factor.

Optionally, one or more of the following steps may also be repeated in the iteration process:

- providing uncalibrated and/or non-calibrated camera data of a camera, wherein the uncalibrated camera data comprise an image of at least a part of a tracking system, e.g. positioned close to a region of interest of the patient, (and/or at least a part of the marker device, at least a part of the region of interest and/or at least a part of a working environment);
- specifying and/or assuming an initial value of a focal length of the camera;
- specifying and/or assuming a working distance value of a distance between the camera and the at least part of the tracking system.

Generally, repeating at least some of the steps of the method in an iteration process may allow to iteratively approximate the true or actual value of the focal length with the adapted value of the focal length. Accordingly, the iteration process may allow to increase an accuracy and/or precision of the determination, estimation and/or approximation of the true value of the focal length by the adapted value of the iteration process.

It should be noted, that the adapted value of the focal length, as determined in one iteration of the iteration process, may be used as initial value of the focal length in a subsequent iteration of the iteration process. Accordingly, as the initial value of the focal length may change in subsequent or consecutive iterations, also the calculated distance value may change in subsequent or consecutive iterations. Further, the assumed working distance value may be constant in some of or all the iterations of the iteration process. Alternatively, however, a separate or independent working distance value may be specified for each iteration of the iteration process.

According to an embodiment of the invention, the iteration process is terminated, if a deviation of the calculated distance value with respect to the specified working distance value reaches and/or falls below a threshold value, particularly a predetermined and/or pre-set threshold value, for the deviation of the calculated distance value with respect to the specified working distance value. Based on such termination criterion, a reasonable trade-off between computing time and a precision or quality, with which the true value of the focal length can be approximated by the adapted value of the focal length, can be made.

According to an embodiment of the invention, calculating the change factor comprises calculating a ratio of the specified working distance value and the calculated distance value. Alternatively or additionally, the change factor correlates with and/or is indicative of a ratio of the specified working distance value and the calculated distance value. Accordingly, the change factor may be given by the ratio of the specified working distance value and the calculated distance value. Alternatively, this ratio may be multiplied by a certain factor and/or an offset may be added to the ratio to calculate the change factor. Generally, the ratio of the specified working distance value and the calculated distance value may provide an indication about how close the adapted value of the focal length is to the actual value of the focal length.

According to an embodiment of the invention, the method further comprises the step of comparing the determined change factor to a clamp factor, wherein the clamp factor is indicative of a maximum allowed value of the change factor, particularly a maximum allowed value of the change factor for a single iteration and/or each iteration of the iteration process. Accordingly, the clamp factor may relate to a threshold value indicative of the maximum allowed value of the change factor for a single iteration and/or each iteration of the iteration process.

According to an embodiment of the invention, the method further comprises the step of reducing the change factor if the determined change factor reaches and/or exceeds the clamp factor. Therein, the change factor may be reduced by a predetermined, pre-set and/or specifiable amount and/or percentage. Further, the change factor may be reduced in a single and/or each iteration of the iteration process, if the determined change factor reaches and/or exceeds the clamp factor in the respective iteration.

Generally, by using and/or applying the clamp factor and/or the corresponding reduction of the change factor, the maximum change of the value of the focal length, i.e. the maximum change of the adapted value of the focal length with respect to the initial value, may be limited, e.g. for a single and/or each iteration of the iteration process. When using the adapted value of the focal length for further purposes or a further application, such as e.g. for adjusting the viewing direction in the graphical representation of the pre-operative image, as described in more detail hereinafter, a restriction of the maximum change per iteration may ensure smooth transitions between various viewing directions. This may increase a comfort in visual perception for a user.

According to an embodiment of the invention, the tracking system comprises a marker device with one or more surfaces, e.g. one or more substantially flat surfaces, wherein at least one optical marker, preferably a plurality of optical markers, is arranged on the one or more surfaces of the marker device. Different surfaces of the marker device, e.g. at least two surfaces of the marker device, may be arranged transverse and/or orthogonal to each other. In other words, the respective surface normal vectors of at least two surfaces may be transverse and/or orthogonal to each other. The one or more markers may be monochromatic markers. Further, one or more of the markers may have a certain pattern and/or code. For example, one or more of the markers may comprise an optical pattern, e.g. similar to a quick response (QR) code. On each surface, at least one marker, preferably at least two or three markers, even more preferably at least four markers, for example four to five markers, may be arranged. This may allow to increase a stability of a tracking of the marker device and/or of the markers arranged thereon. Generally, the marker device may be arbitrarily shaped, such as e.g. box-like, rectangular, polygonal, cuboidal, and/or trapezoidal. Further, the marker device may be arranged on and/or attached to an instrument, such as e.g. a surgical instrument. Accordingly, the marker device may be configured and/or arranged to be moved, particularly manually moved, by a user, e.g. a medical doctor during a surgery.

For tracking purposes, it may be sufficient that the marker device comprises at least one marker on at least one surface of the marker device, wherein a geometry of the marker may preferably be known. If a plurality of markers is arranged on the marker device, a geometry of each of the markers and/or a geometry of the markers with respect to each other may be known and/or pre-determined.

According to an embodiment of the invention, the method further comprises the following steps:
detecting one or more optical markers arranged on one or more surfaces of a marker device of the tracking system based on the adapted focal length value and based on the uncalibrated camera data; and
determining a position of a reference point of the marker device, particularly a position of a tip of the marker device, with respect to and/or relative to the camera (and/or a position of the camera). Alternatively or additionally an orientation of the marker device of the tracking system with respect to the camera (and/or a position of the camera) may be determined.

Generally, by using the adapted focal length value for detecting the one or more optical markers a precision, stability and/or reliability of the detection of the one or more markers may be increased. Further, using the adapted focal length may allow to use the uncalibrated camera data without knowing the actual optical properties of the camera, particularly the actual value of the focal length. In turn, this allows retrofitting the inventive method to existing hardware in an operating room, thereby significantly reducing installation cost and/or effort.

It should be noted that a plurality of optical markers can be detected substantially simultaneously. This may further allow increasing a stability, reliability and/or precision of the determination of the reference point of the marker device and/or the orientation of the marker device with respect to the camera.

Therein, the reference point of the marker device may refer to an arbitrary reference point of the marker device, such as e.g. an edge, a border and/or a tip of the marker device, relative to the position of the camera. Such reference points may be determined with high accuracy and/or precision. Further, the determined reference point may refer to a point in three-dimensional space in an arbitrary coordinate or reference system, e.g. in which the position of the camera is known. The position of the camera may refer to a reference position of the camera, such as, e.g. an edge and/or a center of the camera. Accordingly, the determined reference point may be given in and/or may comprise three spatial coordinates relative to the position of the camera.

Further, the orientation of the marker device of the tracking system with respect to the camera may refer to an orientation of an axis of the marker device, e.g. a longitudinal axis, and/or any other geometrical feature of the marker device, such as e.g. an edge, with respect to the camera and/or with respect to the position of the camera. The orientation of the marker device may be given as a vector in three-dimensional space in an arbitrary coordinate or reference system, e.g. in which the position of the camera is known.

According to an embodiment of the invention, the method further comprises the steps of determining tracking data of the tracking system and/or the marker device based on the detected one or more optical markers of the tracking system, wherein the tracking data are indicative of and/or comprise information about a position of the reference point of the marker device with respect to the camera and/or the position of the camera.

Alternatively or additionally, the tracking data are indicative of and/or comprise information about the determined orientation of the marker device of the tracking system with respect to the camera and/or the camera.

According to an embodiment of the invention, the method further comprises:
displaying, on a graphical user interface and/or a display, a graphical representation of a pre-operative image of at least a part of the patient; and
adjusting a viewing direction of the graphical representation of the pre-operative image based on the determined position of the reference point of the marker device and/or based on the determined orientation of the marker device with respect to the camera.

Therein, pre-operative image may refer to a three-dimensional image, three-dimensional image data and/or a three-dimensional image data set of the at least part of the patient. The pre-operative image may be determined in a pre-operative scan of the patient using any suitable imaging modality. For instance, the pre-operative image may refer to a computed tomography (CT) scan or image, a magnetic resonance (MR) scan or image, a three-dimensional ultrasound scan or image, or the like.

Further, the viewing direction may refer to a direction of a virtual view in the graphical representation of the pre-operative image as displayed on the graphical user interface. Therein, the viewing direction may be centered on a part or body part of the patient and/or on a center of view. The center of view may be defined by and/or may be derived from the determined position of the reference point of the marker device. Apart from that, the viewing direction may be defined by and/or may be derived from the determined orientation of the marker device.

Generally, adjusting the viewing direction of the graphical representation of the pre-operative image based on the determined position and/or orientation of the marker device may allow a user to interactively change and/or adapt the viewing direction and/or the center of view in the graphical representation by moving, translating and/or rotating the marker device, e.g. manually. Accordingly, the user may not have to navigate through the graphical representation by actuating any actuating element, e.g. on the graphical user interface. This may be particularly advantageous in view of clinical hygienic standards. Also, an efficiency of a process of navigating through the pre-operative image or the graphical representation thereof may be significantly increased, e.g. when compared to a situation, where the navigation is done by actuating an actuating element, e.g. on the graphical user interface. This may further safe time in the overall procedure, e.g. a surgery, that the user may have to perform on the patient.

According to an embodiment of the invention, the viewing direction of the graphical representation is adjusted according and/or corresponding to the orientation of the marker device with respect to the camera. By way of example, a vector describing the orientation of the marker device and/or tracking data indicative of the orientation of the marker device may be used to derive and/or may define the viewing direction in the graphical representation. Accordingly, the viewing direction in the graphical representation may correlate with the determined orientation of the marker device. In other words, the determined orientation of the marker device may be translated to the viewing direction. Therein, the graphical representation may be displayed along this viewing direction.

According to an embodiment of the invention, the method further comprises:
providing further uncalibrated camera data of the camera, wherein the further uncalibrated camera data comprise a further image of the at least part of the tracking system;
detecting the one or more optical markers of the marker device of the tracking system based on the further uncalibrated camera data;
determining a further orientation of the marker device of the tracking system with respect to the camera based on the further uncalibrated camera data; and
determining an orientation change of the marker device, the orientation change being indicative of a change of the further orientation of the marker device, as determined based on the further uncalibrated camera data, with respect to the determined orientation of the marker device, as determined based on the uncalibrated camera data.

The uncalibrated camera data and the further uncalibrated camera data may each refer to an image captured and/or acquired by the camera at two different instants of time. Accordingly, the uncalibrated camera data may be acquired at a first time and the further uncalibrated may be acquired at a second time, which differs from the first time. In other words, the uncalibrated camera data and the further uncalibrated camera data may refer to a sequence and/or time-series of images (or uncalibrated camera data) as acquired and/or captured by the camera. The orientation of the marker device may change between the first time and the second (and/or between the uncalibrated camera data and the further uncalibrated camera data), e.g. due to a movement, translation and/or rotation of the marker device by the user. The orientation change and/or change in the orientation of the marker device may then be determined and e.g. subsequently used for adjusting the viewing direction in the graphical representation. Generally, the orientation change may be determined e.g. based on a ratio and/or a difference of the orientation of the orientation and the further orientation of the marker device. By way of example, the orientation change may be indicative of and/or correlate with a movement and/or rotation of the marker device by a certain angle.

According to an embodiment of the invention, the method further comprises the step of translating the determined orientation change of the marker device into a viewing change of the viewing direction of the graphical representation of the pre-operative image. Accordingly, based on the determined orientation change, the viewing change in the graphical representation may be determined and/or calculated. By way of example, a movement and/or rotation of the marker device by a certain angle, as described by the orientation change, may be translated into the viewing change, which may be indicative of and/or correlate with a change of the viewing angle in the graphical representation.

According to an embodiment of the invention, the determined orientation change is translated into the viewing change based on weighting the determined orientation change with a weighting factor, such that the viewing change is increased or decreased relative to the orientation change. Accordingly, by means of the weighting factor, the orientation change may be amplified or mitigated to provide the viewing change. Thus, the weighting factor may serve to adapt a sensitivity of an adjustment of the viewing direction in response to a movement and/or rotation of the marker device. By way of example, a movement/rotation of the marker device by a first angle may be translated, by applying the weighting factor, e.g. by multiplying the orientation change with the weighting factor, into a viewing angle corresponding to a second angle larger than the first angle. In other words, a small movement/rotation of the marker device may cause a large change of the viewing direction. This allows e.g. to change the viewing direction by an angle of up to and even more than about 180° by rotating the marker device by less than about 180°. Alternatively, a movement/rotation of the marker device by a first angle may be translated, by applying the weighting factor, e.g. by multiplying the orientation change with the weighting factor, into a viewing angle corresponding to a second angle less than the first angle. Accordingly, a large movement/rotation of the marker device may cause a small change of the viewing direction. This may allow to precisely adjust the viewing direction by means of moving/rotating the marker device. Overall, the weighting factor may allow to control that a rotation/movement of the marker device can cause a subtle or strong rotation in the graphical representation and/or in a virtual view of the pre-operative image. By way of example, a value of the weighting factor may be specifiable and/or adjustable by the user, e.g. by actuating a slider on a graphical user interface.

According to an embodiment of the invention, the method further comprises the step of registering a longitudinal axis of the patient based on pointing, e.g. sequentially pointing, at least a part of the tracking system, particularly a marker device of the tracking system, to at least two longitudinal points on the patient, wherein the at least two longitudinal points are spaced apart from each other in a direction parallel to the longitudinal axis of the patient. Alternatively or additionally, the method further comprises the step of registering a transverse axis of the patient based on pointing, e.g. sequentially pointing, at least a part of the tracking system, particularly a marker device of the tracking system, to at least two transverse points on the patient, wherein the at least two transverse points are spaced apart from each other in a direction parallel to the transverse axis of the patient. Such registration of the longitudinal and/or the transverse axis of the patient may serve to determine the main directions of the patient, e.g. the four main directions, i.e. top, bottom, left, right. This may allow to adjust and/or align an overall orientation of the pre-operative image with respect to the longitudinal and/or transverse axis of the patient. It should be noted that the registration of the longitudinal and/or the transverse axis may be performed once, e.g. prior to an actual surgery. By way of example, the marker device and/or an instrument, on which the marker device may be arranged, may be pointed to four points on the patient's skin, wherein those four points may form and/or define the main directions of the patient. Further, the registration of the longitudinal and/or transverse axis may be bound to patient reference of the tracking system, which patient reference may be arranged close to and/or nearby the patient, e.g. at a fixed position relative to the patient. This allows to detect and/or compensate movements of the patient during a surgery and to adapt the graphical representation accordingly, e.g. if the patient is shifted during the surgery by moving the couch or patient support, on which the patient may be arranged. Therein, the patient reference of the tracking system may comprise at least one surface, e.g. a substantially flat surface, and/or at least one optical marker.

In a second aspect, the invention is directed to a program, program element and/or a computer program which, when running on at least one processor (for example, a processor) of at least one computer (for example, a computer), when running on a computer, or when loaded onto a computer, e.g. into at least one memory (for example, a memory) of at least one computer (for example, a computer), causes the at least one computer to perform the method according to the first aspect, as described above and in the following.

The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect, as described above and in the following.

A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore may alternatively or additionally relate to a data stream representative of the aforementioned program.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:
  a) the at least one computer according to the fourth aspect;
  b) at least one electronic data storage device storing at least the uncalibrated camera data; and
  c) a medical device for carrying out a medical procedure on the patient, wherein the at least one computer is operably coupled to
    the at least one electronic data storage device for acquiring, from the at least one data storage device, at least the uncalibrated camera data, and
    the medical device for issuing a control signal to the medical device for controlling the operation of the medical device, e.g. on the basis of the uncalibrated camera data and/or the adapted value of the focal length, as described above and in the following.

According to an embodiment of the invention, the medical device comprises a graphical user interface for displaying a graphical representation of a pre-operative image of at least a part of the patient, wherein the at least one computer is operably coupled to the graphical user interface for controlling a viewing direction of the graphical representation based on the calculated adapted value of the focal length of the camera.

The present invention also relates to the use of any of the first to fifth aspect. Particularly, the invention also relates to the use of the method according to the first aspect, the program according to the second aspect, the computer-readable medium according to the third aspect and/or the computer according to the fourth aspect in the medical system or any embodiment thereof according to the fifth aspect.

It is emphasized that features, functions, elements and/or steps, which are described above and in the following with reference to one aspect of the invention, equally apply to any other aspect of the invention described above and in the following. Particularly, features and/or steps, as described above and in the following with reference to the method according to the first aspect, equally apply the computer program according to the second aspect, to the computer-readable medium according to the third aspect, to the computer according to the fourth aspect and/or to the medical system according to the fifth aspect, and vice versa.

These and other aspects of the invention will be apparent from and elucidated with reference to the embodiments described hereinafter.

Definitions

In this section, definitions for specific terminology used in this disclosure are provided which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

According to the present disclosure, the terms acquiring data and retrieving data may be used synonymously. The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Registering

The n-dimensional image of a body is registered when the spatial location of each point of an actual object within a space, for example a body part in an operating theatre, is assigned an image data point of an image (CT, MR, etc.) stored in a navigation system.

Image Registration

Image registration is the process of transforming different sets of data into one coordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

Marker

It is the function of a marker (e.g. an optical marker) to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

Marker Device

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

Marker Holder

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

Pointer

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

Navigation System

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:
  a computer for processing the absolute point data and the relative point data;
  a detection device for detecting the position of the main and auxiliary points in order to generate the absolute point data and to supply the absolute point data to the computer;
  a data interface for receiving the relative point data and for supplying the relative point data to the computer; and
  a user interface for receiving data from the computer in order to provide information to the user, wherein the received data are generated by the computer on the basis of the results of the processing performed by the computer.

Surgical Navigation System

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Imaging Methods

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

BRIEF DESCRIPTION OF THE DRAWINGS

In the following, the invention is described with reference to the appended figures which give background explanations and represent specific embodiments of the invention.

The scope of the invention is however not limited to the specific features disclosed in the context of the figures, wherein.

The figures are schematic only and not true to scale. In principle, identical or like parts, elements and/or steps are provided with identical or like reference symbols in the figures.

DESCRIPTION OF EMBODIMENTS

Figure 1:
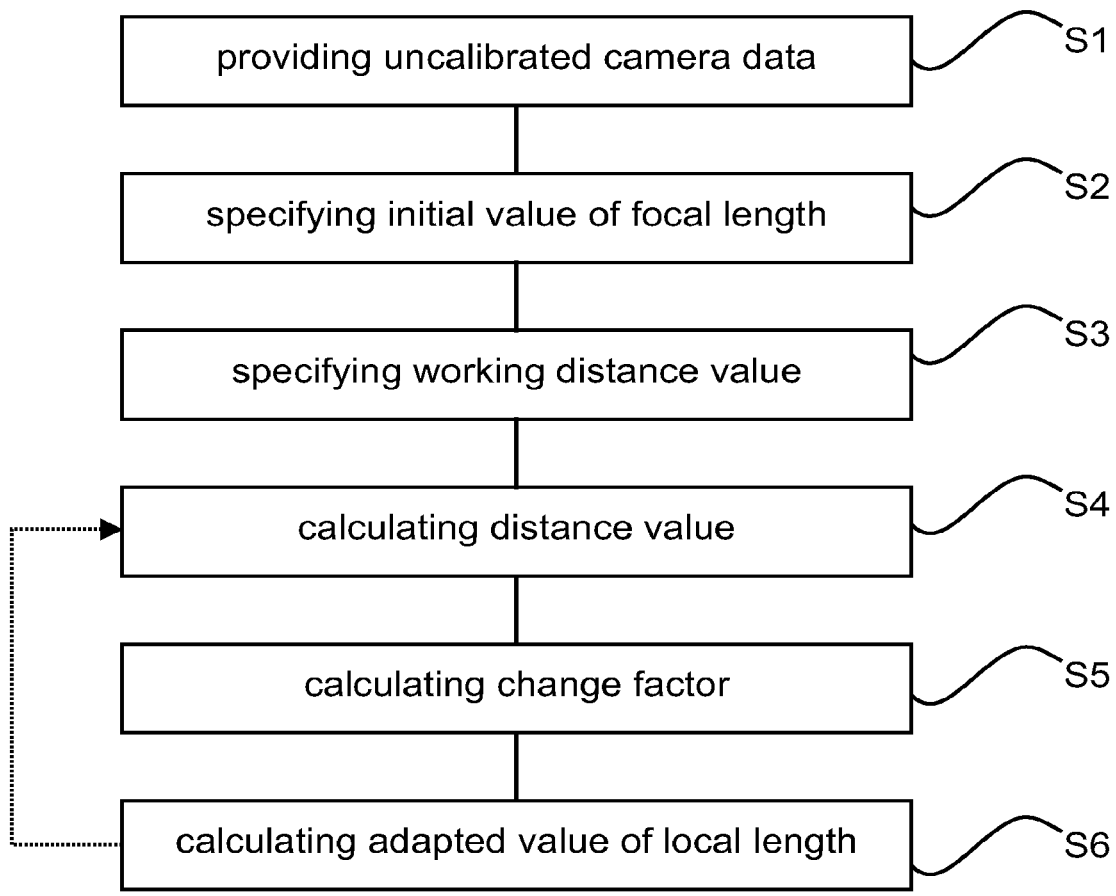
FIG. 1 shows a flowchart illustrating steps of a method of determining a focal length of a camera and/or of adjusting a viewing direction in a graphical representation of a pre-operative image of at least a part of a patient according to an exemplary embodiment of the invention.

FIG. 1 shows a flowchart illustrating steps of a method of determining a focal length of a camera and/or of adjusting a viewing direction in a graphical representation of a pre-operative image of at least a part of a patient according to an exemplary embodiment of the invention.

Step S1 comprises providing uncalibrated camera data of a camera, wherein the uncalibrated camera data comprise an image of at least a part of a tracking system, e.g. positioned close to and/or adjacent to a region of interest of the patient.

Step S2 comprises specifying and/or assuming an initial value of a focal length of the camera, and step S3 comprises specifying and/or assuming a working distance value of a distance between the camera and the at least part of the tracking system.

Further, step S4 comprises calculating a distance value of the distance between the camera (and/or a position of the camera) and the at least part of the tracking system, e.g. an orthogonal and/or shortest distance between the camera and the at least part of the tracking system, based on the uncalibrated camera data and based on the specified initial value of the focal length of the camera.

Step S5 comprises calculating a change factor based on the specified working distance value and based on the calculated distance value. Therein, calculating the change factor may, optionally, comprise calculating a ratio of the specified working distance value and the calculated distance value. Accordingly, the change factor may correlate with the ratio of the specified working distance value and the calculated distance value.

Optionally, step S5 may further comprise comparing the determined change factor to a clamp factor, wherein the clamp factor is indicative of a maximum allowed value of the change factor. Further, step S5 may optionally comprise the step of reducing, e.g. by a predetermined amount or percentage, the change factor if the determined change factor reaches and/or exceeds the clamp factor.

Further, step S6 comprises calculating an adapted value of the focal length of the camera based on the initial value of the focal length and based on the change factor.

As indicated by the dotted arrow in FIG. 1, at least steps S4, S5, and S6 may be repeated in an iteration process. Optionally, also one or more of steps S1, S2, and S3 may be repeated in the iteration process.

Apart from that, step S4 and/or step S5 may, optionally, comprise the steps of determining a deviation of the calculated distance value with respect to the specified working distance value and comparing the determined deviation to a threshold value, particularly a predetermined threshold value, for the deviation of the calculated distance value with respect to the specified working distance value.

The iteration process, as indicated by the dotted arrow in FIG. 1, may, for example, be terminated, if the deviation of the calculated distance value with respect to the specified working distance value, as optionally determined in step S4 and/or S5, reaches and/or falls below a threshold value, particularly a predetermined threshold value, for the deviation of the calculated distance value with respect to the specified working distance value. In other words, the change factor and/or the adapted focal length value may be calculated if, particularly only if, the determined deviation reaches and/or exceeds the threshold value. Otherwise, the iteration process may be terminated.

Figure 2:
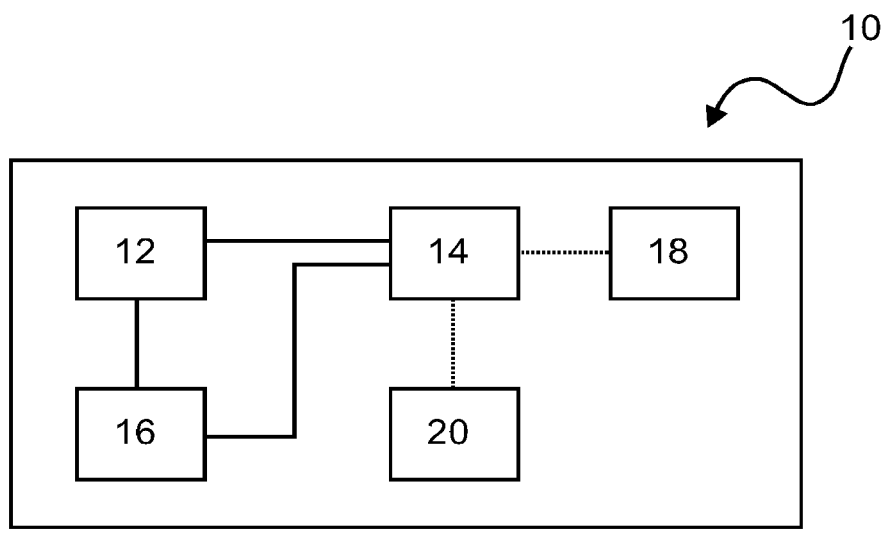
FIG. 2 schematically shows a medical system according to an exemplary embodiment of the invention.

FIG. 2 shows schematically a medical system 10 according to an exemplary embodiment of the invention and/or according to the fifth aspect. The system is in its entirety identified by reference numeral 10 and comprises a camera 12, an uncalibrated camera 12 and/or a camera 12 that is configured to provide two-dimensional uncalibrated camera data.

The medical system 10 further comprises a computer 14, an electronic data storage device (such as a hard disc) 16 for storing at least the uncalibrated camera data acquired by the camera 12. The computer 14 may be coupled to one or both of the storage device 16 and the camera 12 in order to retrieve and/or process the uncalibrated camera data.

The medical system 10 further comprises a medical device 18, e.g. for carrying out a medical procedure. The components of the medical system 10 have the functionalities and properties explained above and in the following with regard to the fifth and/or any other aspect of the present disclosure.

The medical device 18 further comprises a graphical user interface 20. On the user interface 18, a graphical representation of a pre-operative image can be displayed and/or visualized.

Particularly, the at least one computer 14 is operably coupled to the at least one electronic data storage 16 device for acquiring, from the at least one data storage device 16, at least the uncalibrated camera data. Further, computer 14 is coupled to the graphical user interface 20 of the medical device 18. Moreover, the computer 14 is coupled to the medical device 18 for issuing a control signal to the medical device 18 for controlling the operation of the medical device 18, e.g. on the basis of the uncalibrated camera data and/or on the basis of the adapted value of the focal length of the camera 12, as described above and in the following with reference to the method and/or the first aspect of the invention.

Figure 3:
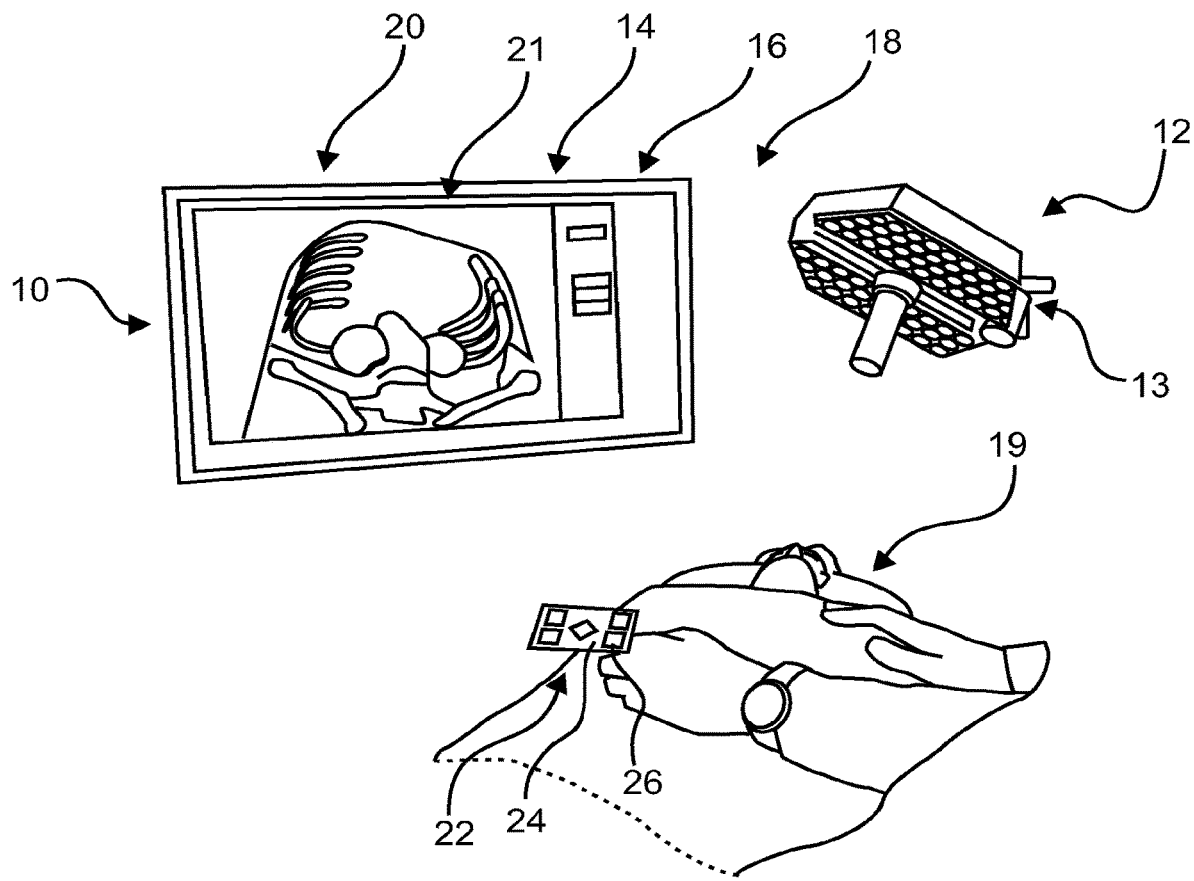
FIG. 3 shows a medical system according to another exemplary embodiment of the invention.
Figure 4:
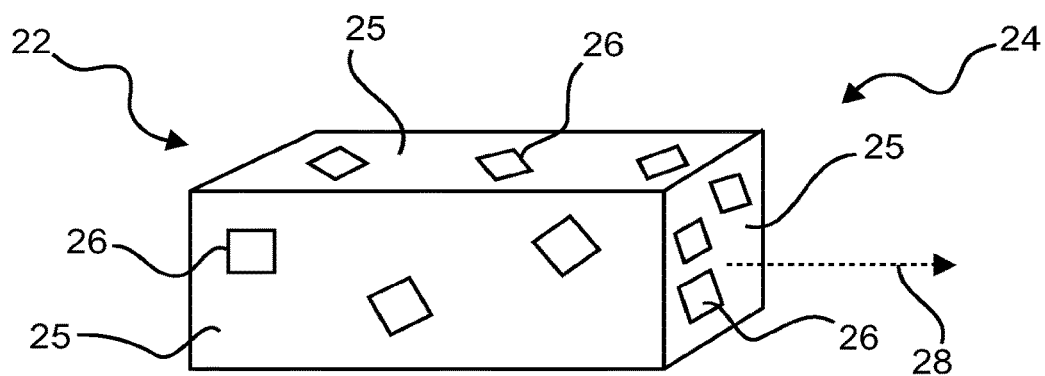
FIG. 4 shows a marker device of the medical system of FIG. 3.

FIG. 3 shows a medical system 10 according to another exemplary embodiment of the invention. If not stated otherwise, the medical system 10 of FIG. 3 comprises the same features as the medical system 10 of FIG. 2. FIG. 4 shows a part of a tracking system 22 and/or a marker device 24 of the medical system 10 of FIG. 3.

In the embodiment depicted in FIG. 3, the data storage device 16 and the computer 14 are integrated in the medical device 18 and/or the graphical user interface 20. The graphical user interface 20 may be wall-mounted. Further, the computer 14 may be configured to receive the uncalibrated camera data and/or a video signal from the camera 12 directly. Alternatively, the uncalibrated camera data may be stored on the data storage device 16 and retrieved by the computer 14 from the data storage device 16. The computer 14 may further be configured to compute the adapted value of the focal length and/or tracking data, as will be explained in more detail in subsequent figures.

On the graphical user interface 20, a graphical representation 21 of a pre-operative image of at least a part of the patient 19 is displayed and/or visualized. In the example shown in FIG. 3, the pre-operative image is a scan of an abdominal region of the patient 19. However, any other part or body part may be displayed on the graphical user interface 20.

Further, the camera 12 comprises a lighting assembly 13, e.g. an array of LEDs arranged around the camera 12 and/or a lens or lens system thereof. The camera 12 may refer to a standard ceiling mounted camera 12. The patient 19 is positioned and/or placed under the camera 12 and/or lighting 13. Exemplary, an abdominal region of the patient may be accessible for the user.

The medical system 10 further comprises a tracking system 22 with a marker device 24. The marker device 24 may be arranged on an instrument, which instrument may be guided with a hand of an operator or user, such that also the marker device 24 is guided by the hand of the user. The marker device 24 comprises a plurality of optical markers 26 arranged on an outer surface of the marker device 24. Particularly, the marker device 24 comprise one or more surfaces 25, e.g. at least two surfaces and/or at least two substantially flat surfaces 25, wherein on each of the surfaces 25 at least one marker 26, preferably a plurality of markers 26, is arranged. The markers 26 may be monochromatic markers 26 and/or each of the markers 26 may comprise an optical pattern.

For example, a plurality of markers 26 can be organized and/or arranged in marker groups, e.g. on each of the surfaces 25. Further, on each of the surfaces 25 at least one and/or at least two, preferably at least three, for example four to five, markers 26 may be arranged. This may ensure that the operator can move the marker device 24 freely in his hand whilst tracking is still possible in any orientation of the marker device 24. On the basis of the detected markers, as described in more detail in subsequent figures, and on the basis of determination of the adapted value of the focal length of the camera 12, as described above and in the following, the medical system 10 can compute a so called pose and/or an orientation 28 of the marker device 24 relative to the camera 12. The orientation 28 of the marker device 24 may, for example, refer to a direction 28 of a longitudinal axis of the marker device 24, as indicated by the dashed arrow in FIG. 4.

For detecting the optical markers 26 by means of the medical system 10 and/or according to the method of the first aspect of the invention, as discussed in more detail in subsequent figures, a data library may be used, which may e.g. be stored on the data storage device 16. Generally, the medical system 10 may be configured to detect a plurality of markers 26 at the same time. This may increase a stability of the tracking.

Generally, with the marker device 24 and/or the instrument in hand, the operator can dynamically adjust a virtual view and/or a viewing direction, e.g. centred to a center of view, such as the abdominal region of the patient 19, as will be explained in more detail in subsequent figures.

Figure 5:
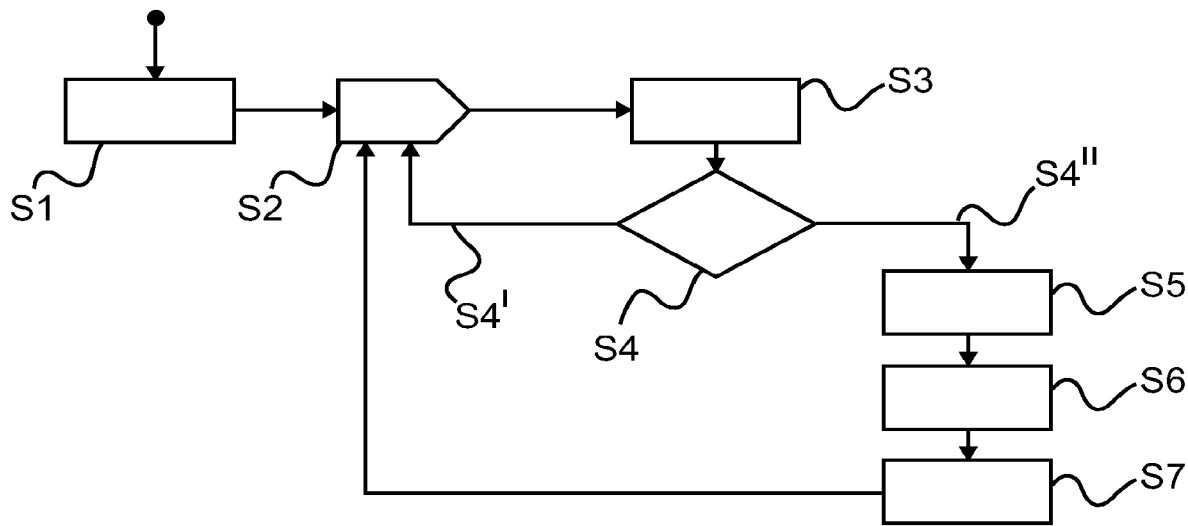
FIG. 5 shows a flowchart illustrating steps of a method of determining a focal length of a camera and/or of adjusting a viewing direction in a graphical representation of a pre-operative image of at least a part of a patient according to an exemplary embodiment of the invention.

FIG. 5 shows a flowchart illustrating steps of a method of determining a focal length of a camera 12 and/or of adjusting a viewing direction in a graphical representation 21 of a pre-operative image of at least a part of a patient according to an exemplary embodiment of the invention. If not stated otherwise, the method of FIG. 5 comprises the same steps as the method of FIG. 1.

Step S1 comprises providing uncalibrated camera data of the camera 12, wherein the uncalibrated camera data comprise an image of at least a part of a tracking system and/or a marker device 24, e.g. positioned close to and/or adjacent to a region of interest of the patient. Further, step S1 comprises specifying and/or assuming a working distance value of the distance between the camera 12 and at least a part of the tracking system 22, e.g. the marker device 24. Further, an initial value of a focal length of the camera 12 may be specified and/or assumed. The initial value of the focal length may have a first component in a first direction and a second component in a second direction, wherein both the first and second direction may be orthogonal to an optical axis of the camera 12. The uncalibrated camera data, the assumed working distance value and the assumed initial value of the focal length may then be provided as input parameters in step S2 for an iteration loop.

In step S3, the uncalibrated camera data may be processed and/or analysed based on the initial value of the focal length. Further, in step S3, a value for the distance between the camera 12 and the marker device 24 is computed and/or derived from the uncalibrated camera data using the initial value of the focal length.

In step S4, the calculated distance value and the specified working distance value are compared, e.g. based on calculating a ratio of these two quantities and/or by subtracting one of the quantities from the other one. Accordingly, a deviation of the working distance value and the calculated distance value may be determined in step S4. Optionally, this deviation may be compared to a threshold value. If the threshold value is not reached, the iteration process may be terminated and the iteration loop may start again at any of steps S1 and S2, wherein further uncalibrated data may be used as input for the next iteration process. This is indicated by reference sign S4' in FIG. 5.

On the other hand, if the threshold value is reached and/or exceeded, the method or iteration process may continue along route S4". Therein, a change factor is calculated in step S5, which change factor may be given as the ratio of the specified working distance value and the calculated distance value.

Optionally, in step S6 the determined change factor may be compared to a clamp factor, wherein the clamp factor is indicative of a maximum allowed value of the change factor, e.g. per iteration. Further, step S5 may optionally comprise the step of reducing the change factor if the determined change factor reaches and/or exceeds the clamp factor.

Finally, in step S7, an adapted value of the focal length is determined, particularly an adapted value of the focal length in a first direction (e.g. an x-direction) and a second direction (e.g. a y direction), wherein both the first and the second direction may be transverse and/or orthogonal to each other and orthogonal to an optical axis of the camera 12. Accordingly, the adapted value of the focal length may comprise a first component which may be given by the product of the first component of the initial value of the focal length and the change factor. Likewise, the adapted value of the focal length may comprise a second component which may be given by the product of the second component of the initial value of the focal length and the change factor.

Figure 6:
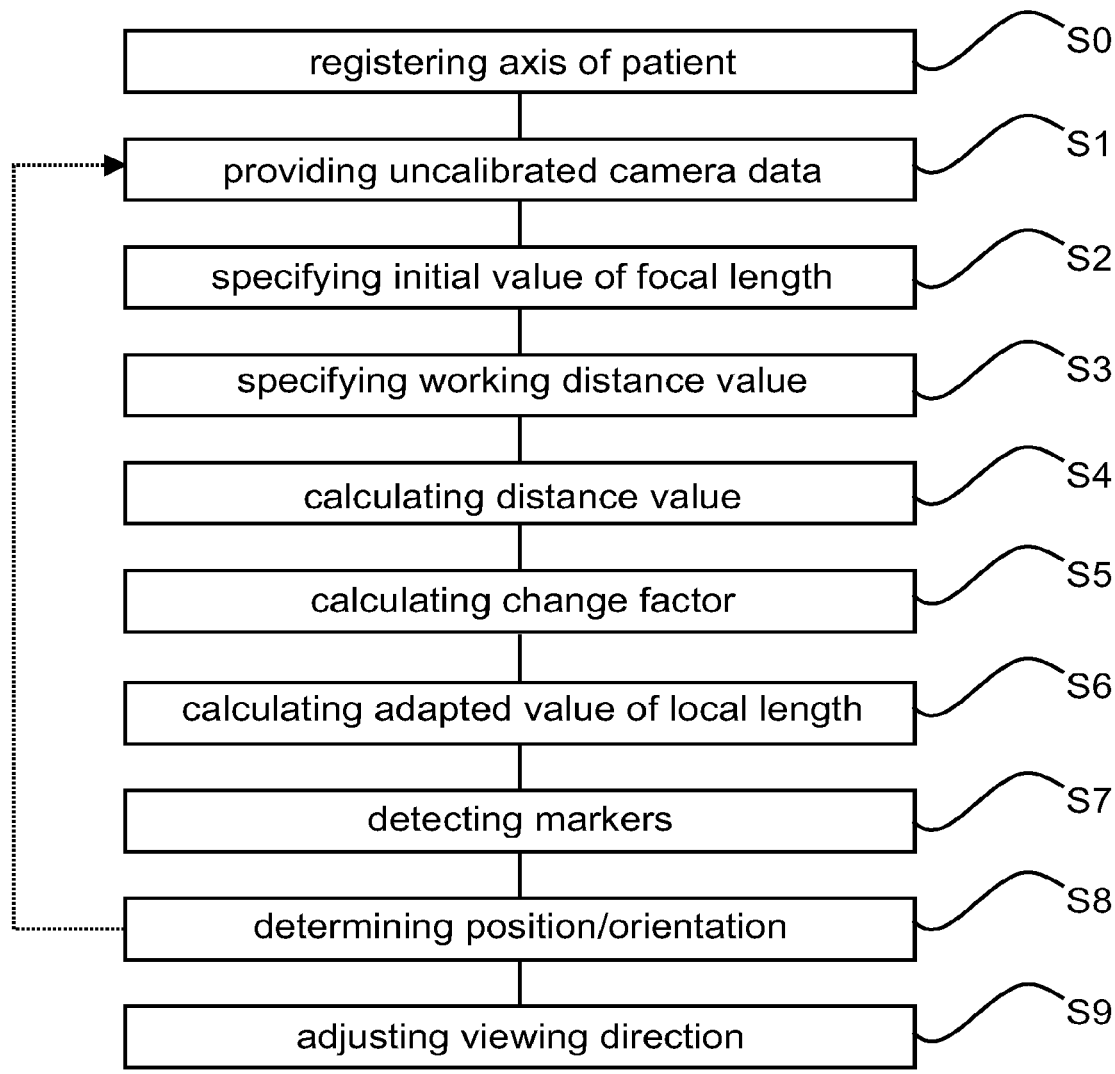
FIG. 6 shows a flowchart illustrating steps of a method of determining a focal length of a camera and/or of adjusting a viewing direction in a graphical representation of a pre-operative image of at least a part of a patient according to an exemplary embodiment of the invention.
Figure 7:
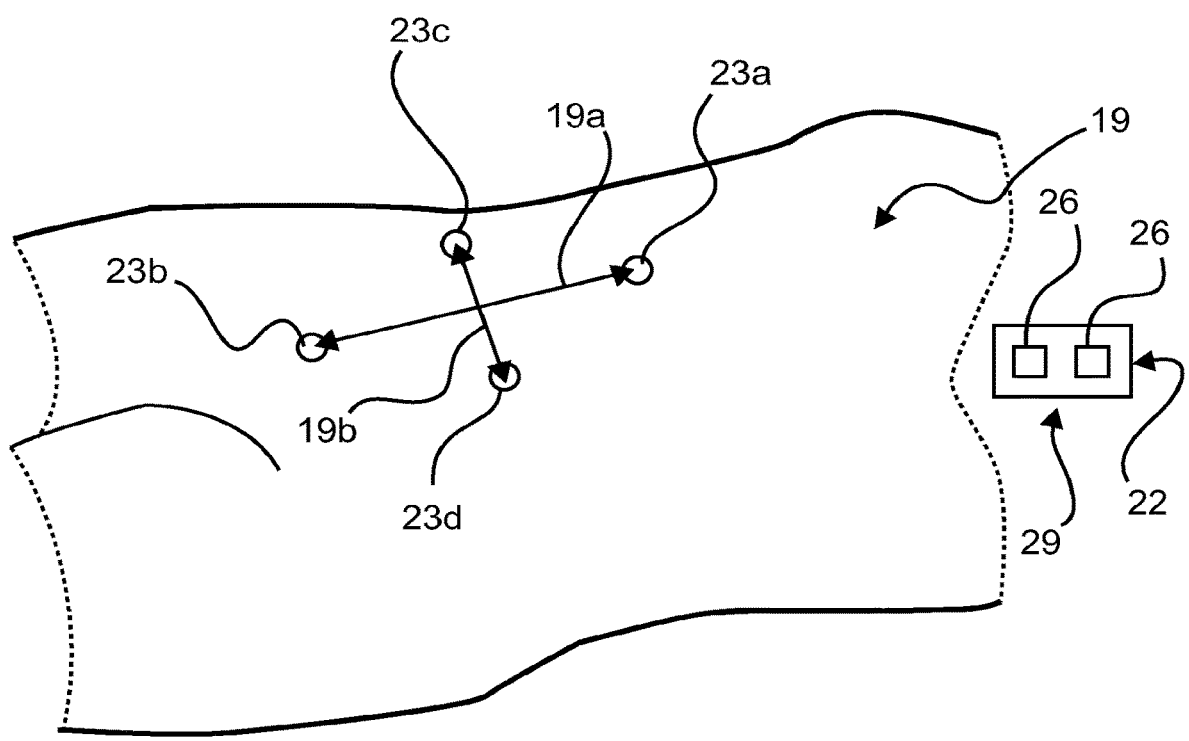
FIG. 7 illustrates a step of the method of FIG. 6.

FIG. 6 shows a flowchart illustrating steps of a method of determining a focal length of a camera and/or of adjusting a viewing direction in a graphical representation 21 of a pre-operative image of at least a part of a patient according to an exemplary embodiment of the invention. If not stated otherwise, the method of FIG. 6 comprises the same steps as the methods of FIGS. 1 and 5. FIG. 7 illustrates a step, particularly step S0, of the method of FIG. 6.

As illustrated in FIG. 7, step S0 comprises registering a longitudinal axis of the patient 19 based on sequentially pointing at least a part of the tracking system 22, particularly a marker device 24 of the tracking system 22, to at least two longitudinal points 23a, 23b on the patient 19, wherein the at least two longitudinal points 23a, 23b are spaced apart from each other in a direction 19a parallel to the longitudinal axis of the patient 19.

Further, step S0 comprises registering a transverse axis of the patient 19 based on sequentially pointing at least a part of the tracking system 22, particularly a marker device 24 of the tracking system 22, to at least two transverse points 23c, 23d on the patient 19, wherein the at least two transverse points 23c, 23d are spaced apart from each other in a direction 19b parallel to the transverse axis of the patient 19.

The registration has the goal to measure the four main directions of the patient 19 in three-dimensional space. To do so, the operator may acquire several single points 23a-d by pointing the marker device 24 to these points 23a-d on the surface of the patient 19. Those points 23a-d may then form the main directions of the patient 19. The obtained registration may be bound to a patient reference 29 of the tracking system 22, which patient reference 29 may be arranged near and/or close to the patient 19 at a fixed relative position to the patient 19. The patient reference 29, in turn, may comprise one or more markers 26, e.g. flat markers 26, which may e.g. be printed on a surface, as schematically shown in FIG. 7.

Steps S1 to S6 substantially correspond to and/or are identical with steps S1 to S6 of the method described with reference to FIG. 1. Further, steps S1 to S6 may further correspond to the steps of the method of FIG. 5. To avoid lengthy repetitions, it is referred to FIGS. 1 and 5 for a description of steps S1 to S6.

Step S7 comprises detecting one or more optical markers 26 arranged on one or more surfaces 25, e.g. substantially flat surfaces 25, of a marker device 24 of the tracking system 22 based on the adapted focal length value and based on the uncalibrated camera data, as determined in step S6.

Step S8 comprises determining a position of a reference point of the marker device 24, particularly a position of a tip, a corner and/or edge of the marker device 24, with respect to the camera 12 and/or determining an orientation 28 of the marker device 24 of the tracking system 22 with respect to the camera 12. Optionally, in step S8, tracking data may be determined based on the detected one or more optical markers 26 of the tracking system 22, wherein the tracking data are indicative of and/or comprise information about the position of the reference point of the marker device 26. Alternatively or additionally, the tracking data are indicative of and/or comprise information about the determined orientation 28 of the marker device 26 with respect to the camera 12.

Step S9 comprises displaying, on a graphical user interface 20, a graphical representation 21 of a pre-operative image of at least a part of the patient 19 and adjusting a viewing direction of the graphical representation 21 of the pre-operative image based on the determined position of the reference point of the marker device 26 and/or based on the determined orientation 28 of the marker device 26 with respect to the camera 12. Therein, the viewing direction of the graphical representation may be adjusted according and/or corresponding to the orientation 28 of the marker device 26 with respect to the camera 12.

As indicated by dashed arrow in FIG. 6, the method may also repeat steps S1 to S8 iteratively. Therein, after finalizing step S8 in one iteration, further uncalibrated camera data may be provided in step S1 of the subsequent iteration, wherein the further uncalibrated camera data comprise a further image of the marker device 24. Based on the further uncalibrated camera data, steps S2 to S6 may be performed, as described above. Further, based on the further uncalibrated camera data, the one or more optical markers 26 of the marker device 24 of the tracking system 22 are detected in step 7, and a further orientation 28 of the marker device 26 of the tracking system 22 with respect to the camera 12 can be determined in step S8.

When steps S1 to S8 are repeated as described hereinabove, an orientation change of the marker device 26 can be determined in step S9, wherein the orientation change is indicative of a change of the further orientation 28 of the marker device 26, as determined based on the further camera data, with respect to the determined orientation 28 of the marker device 26, as determined based on the camera data.

Moreover, the determined orientation change of the marker device 26 may then be translated in step S9 into a viewing change of the viewing direction of the graphical representation 21 of the pre-operative image. Therein, the determined orientation change may be translated into the viewing change based on weighting the determined orientation change with a weighting factor, such that the viewing change is increased or decreased relative to the orientation change.

Finally, the viewing direction of the graphical representation 21 and/or a center of view may be adjusted in step S9, as described above.

Generally, by determining the position of the reference point of the marker device 26 and the orientation 28 of the marker device 26, the user can adjust the direction or viewing direction of his virtual view (and/or of the graphical representation 21) relative to a region of interest of the patient 19, e.g. an abdominal region of the patient 19. By moving, translating and/or rotating the marker device 26 in hand, the viewing direction, which can be centered on a specific part of the patient, can then be changed interactively by the user.

Further, as described above, by means of the weighting factor, a sensitivity of the change in the viewing direction can be adapted. In this sense, the weighting factor can control that a normal rotation of the instrument can cause a subtle or a strong rotation of the virtual view and/or the graphical representation 21.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A computer-implemented method of determining a focal length of a camera, the method comprising:
    providing uncalibrated camera data of a camera, wherein the uncalibrated camera data comprise an image of at least a part of a tracking system;
    specifying an initial value of a focal length of the camera;
    specifying a working distance value of a distance between the camera and the at least part of the tracking system;
    calculating a distance value of the distance between the camera and the at least part of the tracking system based on the uncalibrated camera data and based on the specified initial value of the focal length of the camera;
    calculating a change factor based on the specified working distance value and the calculated distance value;
    calculating an adapted value of the focal length of the camera based on the initial value of the focal length and based on the change factor;
    detecting one or more optical markers arranged on one or more surfaces of a marker device of the tracking system based on the adapted focal length value and based on the uncalibrated camera data; and
    determining a position of a reference point of the marker device, particularly a position of a tip of the marker device, with respect to the camera; and/or
    determining an orientation of
    the marker device of the tracking system with respect to the camera.

2. The method according to claim 1, wherein calculating the distance value comprises:
    determining a deviation of the calculated distance value with respect to the specified working distance value; and
    comparing the determined deviation to a threshold value for the deviation of the calculated distance value with respect to the specified working distance value.

3. The method according to claim 1, wherein at least the calculating of the distance value, the calculating of the change factor, and the calculating of the adapted value are repeated in an iteration process.

4. The method according to claim 3, wherein the iteration process is terminated, if a deviation of the calculated distance value with respect to the specified working distance value reaches and/or falls below a threshold value for the deviation of the calculated distance value with respect to the specified working distance value.

5. The method according to claim 1, wherein calculating the change factor comprises calculating a ratio of the specified working distance value and the calculated distance value, and/or wherein the change factor correlates with and/or is indicative of a ratio of the specified working distance value and the calculated distance value.

6. The method according to claim 1, further comprising comparing the determined change factor to a clamp factor, wherein the clamp factor is indicative of a maximum allowed value of the change factor.

7. The method according to claim 6, further comprising reducing the change factor if the determined change factor reaches and/or exceeds the clamp factor.

8. The method according to claim 1, wherein the tracking system comprises a marker device with at least one surface, wherein at least one optical marker is arranged on the surface of the marker device.

9. The method according to claim 1, further comprising:
    displaying, on a graphical user interface, a graphical representation of a pre-operative image of at least a part of a patient; and
    adjusting a viewing direction of the graphical representation of the pre-operative image based on the determined position of the reference point of the marker device and/or based on the determined orientation of the marker device with respect to the camera.

10. The method according to claim 9, wherein the viewing direction of the graphical representation is adjusted according and/or corresponding to the orientation of the marker device with respect to the camera.

11. The method according to claim 1, further comprising:
    providing further uncalibrated camera data of the camera, wherein the further uncalibrated camera data comprise a further image of the at least part of the tracking system;
    detecting the one or more optical markers of the marker device of the tracking system based on the further uncalibrated camera data;
    determining a further orientation of the marker device of the tracking system with respect to the camera based on the further uncalibrated camera data; and
    determining an orientation change of the marker device, the orientation change being indicative of a change of the further orientation of the marker device, as determined based on the further camera data, with respect to the determined orientation of the marker device, as determined based on the camera data.

12. The method according to claim 11, further comprising translating the determined orientation change of the marker device into a viewing change of the viewing direction of the graphical representation of the pre-operative image.

13. The method according to claim 12, wherein the determined orientation change is translated into the viewing change based on weighting the determined orientation change with a weighting factor, such that the viewing change is increased or decreased relative to the orientation change.

14. The method according to claim 13, further comprising:
    registering a longitudinal axis of the patient based on pointing at least a part of the tracking system to at least two longitudinal points on the patient, wherein the at least two longitudinal points are spaced apart from each other in a direction parallel to the longitudinal axis of the patient; and/or registering a transverse axis of the patient based on pointing at least a part of the tracking system to at least two transverse points on the patient, wherein the at least two transverse points are spaced apart from each other in a direction parallel to the transverse axis of the patient.

15. The method according to claim 14, wherein the camera is a standard operating room camera, and/or wherein the camera is a two-dimensional camera.

16. A non-transitory computer readable storage medium storing a program, that when executed on at least one processor of a computer or loaded onto the at least one processor of the computer, causes the computer to perform a method comprising:

providing uncalibrated camera data of a camera, wherein the uncalibrated camera data comprise an image of at least a part of a tracking system;

specifying an initial value of a focal length of the camera;

specifying a working distance value of a distance between the camera and the at least part of the tracking system;

calculating a distance value of the distance between the camera and the at least part of the tracking system based on the uncalibrated camera data and based on the specified initial value of the focal length of the camera;

calculating a change factor based on the specified working distance value and the calculated distance value;

calculating an adapted value of the focal length of the camera based on the initial value of the focal length and based on the change factor;

detecting one or more optical markers arranged on one or more surfaces of a marker device of the tracking system based on the adapted focal length value and based on the uncalibrated camera data; and determining a position of a reference point of the marker device, particularly a position of a tip of the marker device, with respect to the camera; and/or determining an orientation of the marker device of the tracking system with respect to the camera.

17. A medical system, comprising:
a) at least one computer configured to:
provide uncalibrated camera data of a camera, wherein the uncalibrated camera data comprise an image of at least a part of a tracking system;
specify an initial value of a focal length of the camera;
specify a working distance value of a distance between the camera and the at least part of the tracking system;
calculate a distance value of the distance between the camera and the at least part of the tracking system based on the uncalibrated camera data and based on the specified initial value of the focal length of the camera;
calculate a change factor based on the specified working distance value and the calculated distance value;
calculate an adapted value of the focal length of the camera based on the initial value of the focal length and based on the change factor;
detect one or more optical markers arranged on one or more surfaces of a marker device of the tracking system based on the adapted focal length value and based on the uncalibrated camera data; and
determine a position of a reference point of the marker device, particularly a position of a tip of the marker device, with respect to the camera; and/or
determine an orientation of the marker device of the tracking system with respect to the camera;
b) at least one electronic data storage device storing at least the uncalibrated camera data; and
c) a medical device for carrying out a medical procedure on the patient,
wherein the at least one computer is operably coupled with
the at least one electronic data storage device for acquiring, from the at least one data storage device, at least the uncalibrated camera data, and
the medical device for issuing a control signal to the medical device for controlling an operation of the medical device.

18. The medical system according to claim 17, wherein the medical device comprises a graphical user interface for displaying a graphical representation of a pre-operative image of at least a part of the patient, wherein the at least one computer is operably coupled with the graphical user interface for controlling a viewing direction of the graphical representation based on the calculated adapted value of the focal length of the camera.

* * * * *